(12) United States Patent
Schäfer et al.

(10) Patent No.: US 10,442,150 B2
(45) Date of Patent: Oct. 15, 2019

(54) MEDICAL APPARATUS COMPRISING AN ANTIMICROBIAL SURFACE COATING AND METHOD FOR CONTROLLING MICROORGANISMS ON THE SURFACE OF SUCH AN APPARATUS

(71) Applicant: B. BRAUN AVITUM AG, Melsungen (DE)

(72) Inventors: Oliver Schäfer, Neuenstein (DE); Christian Schleicher, Dipperz (DE)

(73) Assignee: B. Braun Avitum AG (DE)

( * ) Notice: Subject to any disclaimer, the term of this patent is extended or adjusted under 35 U.S.C. 154(b) by 152 days.

(21) Appl. No.: 15/499,093

(22) Filed: Apr. 27, 2017

(65) Prior Publication Data

US 2017/0321067 A1 Nov. 9, 2017

(30) Foreign Application Priority Data

May 3, 2016 (DE) .................... 10 2016 108 198

(51) Int. Cl.
*B32B 1/02* (2006.01)
*A61M 1/14* (2006.01)
(Continued)

(52) U.S. Cl.
CPC ............... *B32B 1/02* (2013.01); *A01N 25/12* (2013.01); *A01N 25/26* (2013.01); *A01N 59/16* (2013.01); *A61M 1/14* (2013.01); *A61M 1/1621* (2014.02); *A61M 1/1645* (2014.02); *A61M 1/1656* (2013.01); *A61M 25/0045* (2013.01); *B32B 1/08* (2013.01); *B32B 27/18* (2013.01);
(Continued)

(58) Field of Classification Search
CPC . B32B 1/02; B32B 1/08; B32B 27/18; A61M 1/14; A61M 1/1621; A61M 25/0045; A61M 2025/0056
See application file for complete search history.

(56) References Cited

U.S. PATENT DOCUMENTS 6,342,212 B1 * 1/2002 Schuette .............. A01N 59/16
424/618
2008/0051493 A1 2/2008 Trogolo et al.
(Continued)

FOREIGN PATENT DOCUMENTS

CN 105368274 A 3/2016
CN 105419559 A 3/2016
(Continued)

OTHER PUBLICATIONS

Extended European Search Report for European Application No. 17168047.3, dated Sep. 22, 2017, including English translation, 21 pages.
(Continued)

*Primary Examiner* — Walter Aughenbaugh
(74) *Attorney, Agent, or Firm* — RatnerPrestia

(57) ABSTRACT

The invention relates to a medical apparatus for extracorporeal blood treatment, comprising an antimicrobial surface coating, wherein the antimicrobial surface coating is a powder coating. It further relates to a method for controlling microbes and microorganisms on a surface of a medical apparatus, wherein a powder coating contains components, in particular additives, with an antimicrobial effect.

5 Claims, 3 Drawing Sheets

(51) Int. Cl.
- *B32B 1/08* (2006.01)
- *B32B 27/18* (2006.01)
- *A61M 1/16* (2006.01)
- *A61M 25/00* (2006.01)
- *A01N 25/26* (2006.01)
- *C09D 5/03* (2006.01)
- *C09D 5/14* (2006.01)
- *A01N 25/12* (2006.01)
- *A01N 59/16* (2006.01)
- *C09D 5/08* (2006.01)
- *A61L 2/08* (2006.01)
- *A61L 2/232* (2006.01)

(52) U.S. Cl.
CPC ............... *C09D 5/03* (2013.01); *C09D 5/033* (2013.01); *C09D 5/08* (2013.01); *C09D 5/14* (2013.01); *A61L 2/087* (2013.01); *A61L 2/088* (2013.01); *A61L 2/232* (2013.01); *A61L 2202/24* (2013.01); *A61L 2420/02* (2013.01); *A61M 2025/0056* (2013.01); *A61M 2205/0238* (2013.01)

(56) References Cited

U.S. PATENT DOCUMENTS

| | | |
|---|---|---|
| 2008/0148994 A1 | 6/2008 | Magnin |
| 2010/0297206 A1 | 11/2010 | Kim et al. |
| 2011/0171062 A1 | 7/2011 | Wolfe |
| 2013/0084319 A1* | 4/2013 | Priewe .................. A61K 38/16 424/402 |

FOREIGN PATENT DOCUMENTS

| | | |
|---|---|---|
| DE | 202005014409 U1 | 12/2005 |
| DE | 10 2005 042 181 | 4/2006 |
| DE | 102014215353 A1 | 2/2016 |
| EP | 2574353 A1 | 4/2013 |
| JP | 10168346 A | 6/1998 |
| WO | WO 2011/130124 | 10/2011 |

OTHER PUBLICATIONS

German Search Report with English language translation for Application No. 10 2016 108 198.1, dated Jan. 11, 2017, 15 pages.

* cited by examiner

MEDICAL APPARATUS COMPRISING AN ANTIMICROBIAL SURFACE COATING AND METHOD FOR CONTROLLING MICROORGANISMS ON THE SURFACE OF SUCH AN APPARATUS

CROSS REFERENCE TO RELATED APPLICATIONS

This application claims priority to German application DE 10 2016 108 198.1 filed May 3, 2016, the contents of such application being incorporated by reference herein.

FIELD OF THE INVENTION

The invention relates to a medical apparatus, in particular for extracorporeal blood treatment, comprising an antimicrobial surface coating, as well as to a method for controlling microorganisms on a surface of a medical apparatus of the invention.

BACKGROUND OF THE INVENTION

The growth and proliferation of microorganisms on surfaces of medical apparatuses are undesired effects, representing a substantial hygiene risk in a corresponding treatment surrounding such as hospitals, laboratories, medical practices and the like and impairing the practical value of such medical apparatuses and objects. As a rule, microorganisms are fought in such environments by corresponding cleaning and disinfection.

DESCRIPTION OF THE RELATED ART

However, it is desired that microorganisms do not spread and settle at all or only in a substantially delayed manner. This objective is pursued also in WO 2011/130124 A1, disclosing a method for immobilizing colorants and antimicrobial agents on plastic surfaces of medical apparatuses. Here, a plastic housing is treated with a plurality of functional groups on which a connecting group and thereon an antimicrobial agent is accumulated. There may occur a detrimental effect which consists in that certain properties of the plastic, such as aging resistance, tensile strength, impact resistance etc., are adversely affected by the incorporation of additives in the plastic matrix.

DE 10 2005 042 181 A1 discloses in this connection a molded body, in particular for apparatus parts, apparatus upper shells, apparatus inner parts, apparatus accessories, apparatus components, impression materials, filling materials for medical apparatuses and/or medical products, which is formed at least in sections so as to be repellent against germ colonization. Further, a medical apparatus comprising at least one molded body of this type as well as a method of producing such a molded body are disclosed. Here, one approach is to design the surface so as to be repellent against germs by means of reducing the adhesion. A further approach is to incorporate biocides in the plastic.

SUMMARY OF THE INVENTION

Starting from the prior art described above, the present invention is based on the object to eliminated the above-mentioned disadvantages, in particular to provide a medical apparatus which has antimicrobial properties and can be manufactured in a simple manner. It is desired that the mechanical properties of the housing material are not adversely affected by the antimicrobial properties.

According to aspects of the invention, this object is achieved by a medical apparatus of the type initially mentioned, wherein the antimicrobial surface coating is a powder coating. In terms of the process, the object is achieved by a method for controlling microbes and microorganisms on a surface of a medical apparatus, in particular a medical apparatus according to aspects of the present invention, wherein the powder coating contains components, in particular additives, with an antimicrobial effect. Such an antimicrobial powder coating prevents the generation and development of microorganisms, in particular of bacteria and fungal cultures, in a particularly simple and effective manner.

According to aspects of the invention, the powder coating may be applied onto an apparatus case of a medical apparatus, whose intended use is in particular in the field of extracorporeal blood treatment. In the context of the invention, the term "microorganisms" may also be understood so as to include viruses. The effect of the antimicrobial surface is based on components (additives) incorporated in the coating, which are highly effective against microorganisms but harmless for a human organism.

As it is a coating in the form of a powder coating applied onto the base material, the properties of the housing which are relevant to its functionality will not be altered. In this connection, these include for instance mechanical properties of the housing material or EMC properties (electromagnetic compatibility) of the parts constituting the housing. This is a further distinction to antibacterial surfaces which are produced, for example, with integrated nanoparticles in plastic. With this principle, also the properties of the base material forming the housing will be impaired.

Advantageous embodiments of the invention are defined in the claims and will be explained in more detail below.

The powder coating may be applied only in or on sections or over the full surface area of the apparatus. By way of example, it may be present only in those areas which are touched by patients or operating staff, such as external areas or operating units. However, it is also within the scope of the invention if the powder coating is applied and formed over the full surface area.

In one embodiment of the invention the powder coating is applied onto a metallic surface. As an alternative or in addition, the medical apparatus may comprise an apparatus case and the powder coating may be at least partially applied onto the apparatus case. It is a special advantage that the invention can be used with metallic housings or housing parts, as an incorporation of microbiologically active substances in the matrix of the material, as it is common practice with plastics, is not possible here or only with a concomitant weakening of the base material.

According to a further embodiment of the invention, the powder coating comprises components, in particular additives, which are emitters of ions and/or radicals. This allows the formation of new ions and/or radicals on a constant basis, preferably permanently, in particular in a continuous fashion and to emit these from the powder coating. The emitted ions and/or radicals attack the metabolic systems of the microorganisms or cells, so that these die away. The antimicrobial powder coating prevents their proliferation in this way. Due to the permanent formation of ions and/or radicals, a significant difference can be quantified with respect to the long-term effect in contrast to other principles such as the use of pure/unbound nanosilver.

The components or additives contained in the powder coating may be in particular organometallic substances having an ionizing effect. By way of example, these additives are organometallic substances having an ionizing and/or photocatalytic effect.

In this connection, additives also referred to as auxiliary agents or admixtures are to be mentioned, i.e. substances which are added in small amounts to products in order to reach or improve certain properties. Here, the additives have the task to permanently anchor the substances with antimicrobial effect in the structure of the carrier material to achieve a long-term effect. Substances with an antimicrobial effect are, for instance, metal colloids made of silver, metal colloids made of copper, titanium dioxide, zinc oxide as a biocide additive, etc., or also antimicrobial oligomers.

The powder coating may in particular comprise carrier substances to which ion emitters and/or catalysts adhere. The term "adhere" is to be understood in this sense inter alia as connected, chemically connected, etc.

It is a special advantage that the powder coating allows to produce a surface finish for instance by a special structure or color design, whereas at the same time the mentioned antimicrobial effect is applied. What is more, apart from the intended antimicrobial effect the powder coating allows to achieve further effects such as corrosion protection, etc.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
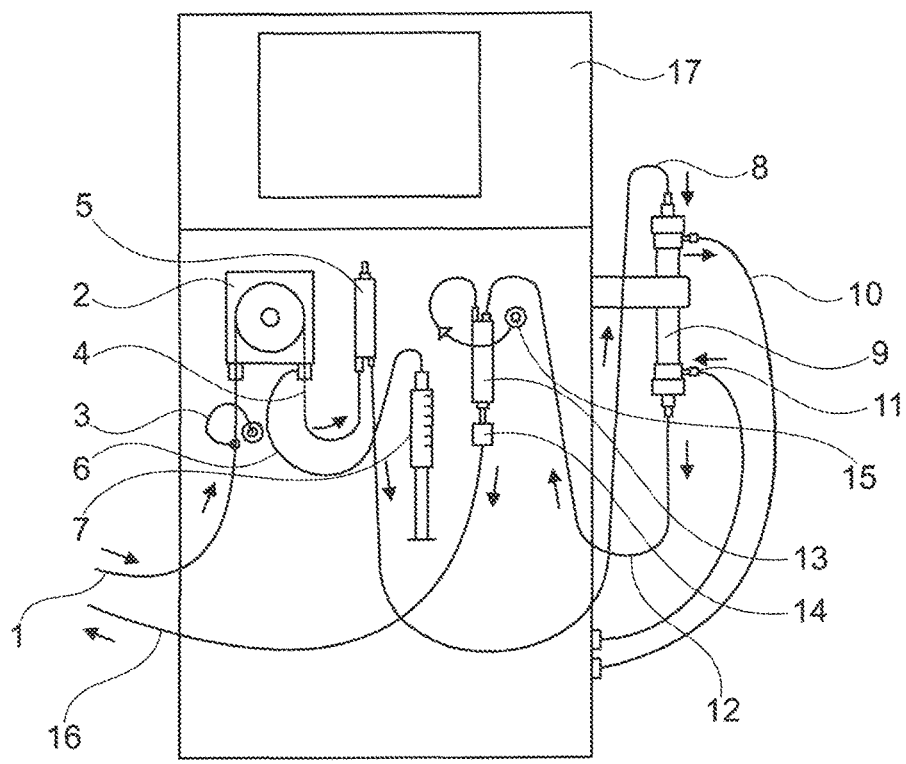
FIG. 1 shows a schematic illustration of a section of a device for extracorporeal blood treatment as an example for a medical apparatus according to aspects of the invention.

Substantially the whole extracorporeal blood circulation system of the device is shown. Said circulation system comprises an arterial blood conduit 1 transporting blood from a patient (not shown) to a peristaltic pump 2 of the treatment device. Upstream of the peristaltic pump 2, an arterial pressure sensor 3 is provided which measures the pressure upstream of the peristaltic pump 2, i.e. the low-pressure side pressure. At the high-pressure side of the peristaltic pump 2, a high-pressure blood conduit 4 extends to an arterial blood collector 5. Directly at the outlet of the peristaltic pump 2, a feed line 6 and a pump 7 allow to add an additive to the blood in the system, e.g. Heparin for blood thinning.

Starting from the arterial blood collector 5, a conduit 8 transports high-pressure blood—which is still untreated and loaded with slag substances—to a dialyzer 9. Said dialyzer has its input side fed with a dialysate via a dialysate feed line 10. In the dialyzer 9, the blood is treated in a known manner with the dialysate, e.g. is cleaned. Used dialysate is discharged from the dialyzer 9 via a dialysate discharge line 11 and is delivered to a (not illustrated) disposal or preparation. Treated blood is conveyed with a blood discharge line 12 from the dialyzer 9 to a venous air collector 13 where air is separated with an air trap 14. Provided on the venous air collector 13 is a venous pressure sensor 15 which detects the venous pressure, i.e. the high-pressure side pressure. Starting from the air trap 14, the treated blood is sent back to the patient via a venous blood conduit 16. FIG. 1 also shows a unit 17 for monitoring and controlling the device. The device for extracorporeal blood treatment is encapsulated in a housing 100 which is at least partially implemented as a molded sheet metal part.

According to aspects of the invention, at least the housing 100 is provided with a powder coating. Said coating may be applied only in sections or over the full surface area. The powder coating may additionally be provided and applied on further units of the device, such as on the control unit 17, for instance.

Figure 2:
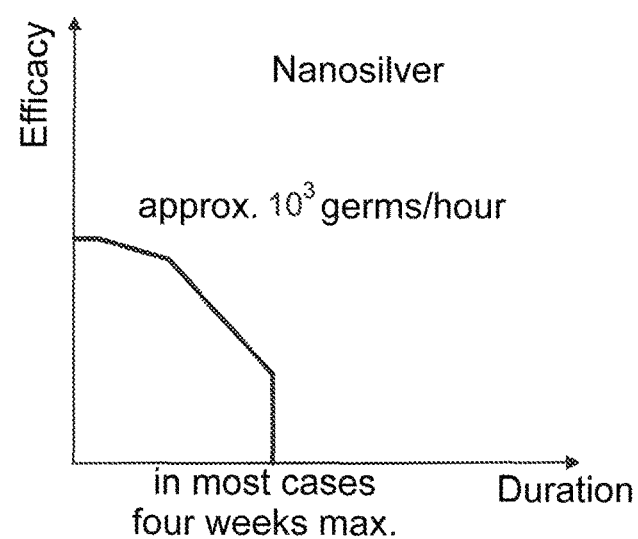
FIG. 2 shows an illustration of the efficacy of nanosilver versus time.
Figure 3:
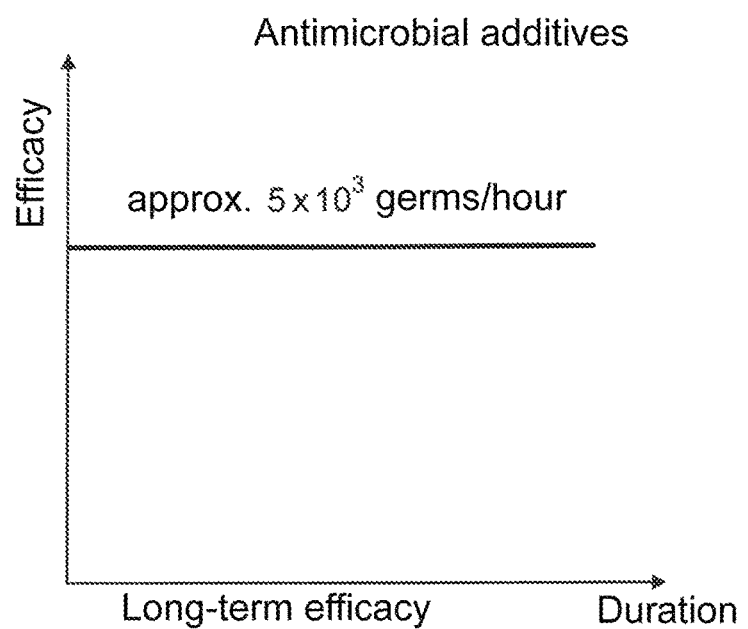
FIG. 3 shows an illustration of the efficacy of antimicrobial additives of the invention versus time.

FIG. 2 shows in a diagram the antimicrobial efficacy of nanosilver. FIG. 3 shows in a similar diagram the antimicrobial efficacy according to aspects of the invention. Here, the abscissa shows the length of time and the ordinate shows the efficacy in each case. It is to be seen that the maximum efficacy of nanosilver is approximately $10^3$ germs per hour, the efficacy of the invention is approximately $5*10^3$ germs per hour. The efficacy of nanosilver drops after a short time in slow fashion first, but then faster and faster and finally comes to a standstill after approximately four weeks. On the other hand, the efficacy according to aspects of the invention lasts for a long period of time and does not decrease.

The antimicrobial effect of nanosilver is based on the formation of silver ions ($Ag+$) on the surface of silver nanoparticles or silver colloids. A remarkable long-term effect can be achieved due to the special ratio between size and surface area of silver colloids. The generated silver ions have a harmful effect on single-cell organisms such as bacteria, yeasts, fungi and viruses in various ways. The strong antimicrobial efficacy of nanosilver is associated to its ability to penetrate cell walls and cell membranes and act in the cell interior. In vitro, colloidal silver is also effective against viruses in that nanosilver particles bind to their surface and suppress the binding of the viruses to host cells. Further antimicrobial metal colloids are copper colloids, for example.

Figure 4:
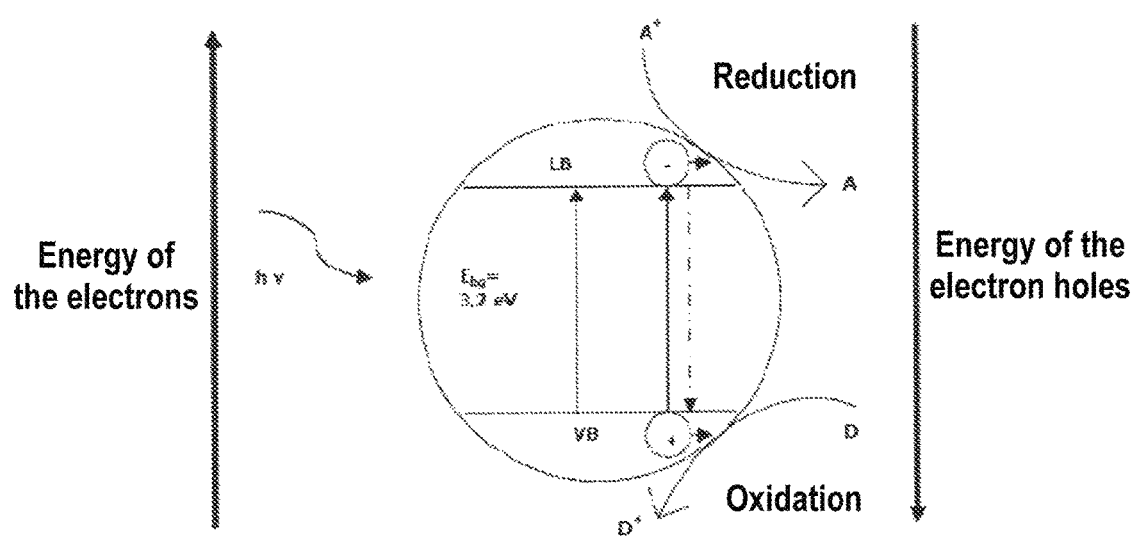
FIG. 4 shows an illustration of a photocatalytic process.

The antimicrobial effect of e.g. nanoparticles made of titanium dioxide is based on a photocatalytic process which causes a steady reaction in combination with light irradiation. In this process, the titanium dioxide acts as a photo catalyst due to a steady photochemical excitation, e.g. by daylight. This results in physical and chemical reactions (reductions, oxidations) (see FIG. 4). In case of titanium dioxide, hydroxyl radicals, superoxide anion radicals and hydrogen peroxide will be generated. The radicals are able to react with organic substances and oxidize them. It is believed that an antimicrobial effect against microorganisms is to be attributed to the hydroxyl radicals.

The antimicrobial effect of antimicrobial oligomers is based on a direct microbicide effect of the antimicrobial oligomers which are able to leave the polymer matrix of the carrier material at a slow rate and in small amounts, hence releasing said microbicide effect in the form of a depot or retard compound. It is preferred that the antimicrobial oligomers are made from one or more monomers selected from the group comprising methacrylic acid-2-tert.-butylaminoethylester, methacrylic acid-2-diethylaminoethylester, methacrylic acid-2-di-ethylaminomethylester, acrylic acid-2-tert.-butylaminoethylester, acrylic acid-3-dimethylaminopropylester, acrylic acid-2-diethylaminoethylester, acrylic acid-2-dimethylaminoethylester, dimethylaminopropylmethacrylamide, diethylamino-propylmethacrylamide, acrylic acid-3-dimethylaminopropylamid, 2-methacryloyloxyethyltrimethylammoniummethosulfate, methacrylic acid-2-diethylaminoethylester, 2-methacryloyloxyethyltrimethylammoniumchloride, 3-methacryloylaminopropyltrimethylammonium-chloride, 2-methacryloyloxyethyltrimethylammoniumchloride, 2-acryloyloxyethyl-4-benzoyldimethylammoniumbromid, 2-methacryloyloxy-ethyl-4-benzoyldimethylammoniumbromid, allyltriphenylphosphoniumbromide, allyltriphenylphosphoniumchloride, 2-acrylamido-2-methyl-1-propane sulfonic acid, 2-diethylaminoethyl-vinylether and/or 3-aminopropylvinylether.

Figure 5A:
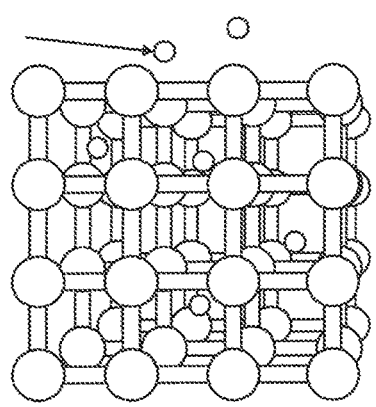
FIGS. 5A and 5B show an illustration of the incorporation of pure/unbound nanoparticles in a grid structure of a carrier material and an illustration of the incorporation of additives binding the antimicrobial active agents in a grid structure of a carrier material.
Figure 5B:
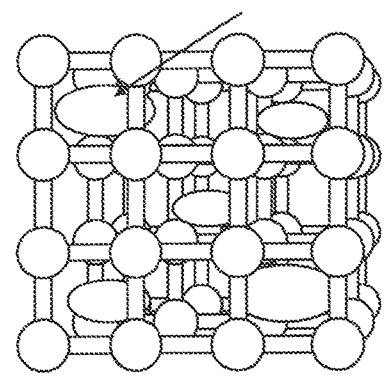

FIGS. 5A and 5B illustrate the incorporation of pure/unbound nanoparticles in a grid structure of a carrier material and the incorporation of additives incorporating the antimicrobial active agents in a grid structure of a carrier material.

The effect mainly consist in the fact that incorporated nanoparticles are able to escape from the grid structure of the carrier material due to their size, whereas the antimicrobial additives incorporate the active agents directly in the grid structure and anchor them in the grid structure of the carrier material due to their size (see FIGS. 5A and 5B).

Here, the microbial efficacy can be achieved both by the photocatalytic principle such as in the example of titanium dioxide and with the antimicrobial effect of metal ions which are generated through metal colloids and continuously emitted to the surroundings. The metal colloids have a size of only few nanometers and a long-term effect can be achieved because of the special ratio between size and surface area. The consumption of the metal to form metal ions is very low. This allows to achieve a long-term effect lasting over several years.

The invention claimed is:

1. A medical apparatus for extracorporeal blood treatment, the medical apparatus comprising:
    a housing; and
    an antimicrobial surface coating on at least a portion of the housing, wherein the antimicrobial surface coating is a powder coating,
    wherein the powder coating comprises components that are emitters of at least one of ions or radicals, and
    wherein the components are organometallic substances having at least one of an ionizing or photocatalytic effect.

2. The medical apparatus according to claim 1, wherein the housing includes a metallic surface and the powder coating is applied onto the metallic surface.

3. The medical apparatus according to claim 1, wherein the components are additives.

4. The medical apparatus according to claim 1, wherein the organometallic substances are oligomers with microbicide action.

5. The medical apparatus according to claim 1, wherein the powder coating comprises carrier substances to which said components adhere.

* * * * *